(12) United States Patent
Zhong et al.

(10) Patent No.: US 12,350,389 B2
(45) Date of Patent: Jul. 8, 2025

(54) FILTERING DEVICE FOR KILLING PATHOGENIC MICROORGANISMS USING DEEP ULTRAVIOLET LASER

(71) Applicant: Guangdong Guozhi Photonics Technology Co., Ltd., Guangdong Province (CN)

(72) Inventors: Chen Zhong, Guangdong Province (CN); Shaowei Zhou, Guangdong Province (CN)

(73) Assignee: Guangdong Guozhi Photonics Technology Co., Ltd., Guangdong (CN)

( * ) Notice: Subject to any disclaimer, the term of this patent is extended or adjusted under 35 U.S.C. 154(b) by 504 days.

(21) Appl. No.: 17/939,495

(22) Filed: Sep. 7, 2022

(65) Prior Publication Data

US 2023/0390435 A1 Dec. 7, 2023

(30) Foreign Application Priority Data

Jun. 7, 2022 (CN) .......................... 202210636259.X

(51) Int. Cl.
*A61L 2/10* (2006.01)
(52) U.S. Cl.
CPC ............. *A61L 2/10* (2013.01); *A61L 2202/11* (2013.01)

(58) Field of Classification Search
CPC ............................... A61L 2/10; A61L 2202/11
See application file for complete search history.

(56) References Cited

U.S. PATENT DOCUMENTS

2012/0168641 A1* 7/2012 Lizotte .................... C02F 1/325
250/503.1

\* cited by examiner

*Primary Examiner* — Sean E Conley

(57) ABSTRACT

A filtering device for killing pathogenic microorganisms using deep ultraviolet laser is provided, including a main body and a deep ultraviolet laser module, the main body is configured for accommodating gas having pathogenic microorganisms; the deep ultraviolet laser module is connected to the main body and configured for totally reflecting the deep ultraviolet laser for multiple times to form a dense and regular deep ultraviolet laser net, such that the gas is filtered in the dense and regular deep ultraviolet laser net to achieve the killing of the pathogenic microorganisms in the gas. The deep ultraviolet laser module includes a deep ultraviolet laser apparatus and a reflection adjusting assembly, the deep ultraviolet laser apparatus is connected to the main body, and the reflection adjusting assembly is configured for adjusting the density of the deep ultraviolet laser net.

9 Claims, 4 Drawing Sheets

FILTERING DEVICE FOR KILLING PATHOGENIC MICROORGANISMS USING DEEP ULTRAVIOLET LASER

CROSS REFERENCE TO RELATED APPLICATION

This patent application claims the benefit and priority of Chinese Patent Application No. 202210636259.X, entitled "FILTERING DEVICE FOR KILLING PATHOGENIC MICROORGANISMS USING DEEP ULTRAVIOLET LASER" filed on Jun. 7, 2022, the disclosure of which is incorporated by reference herein in its entirety as part of the present application.

TECHNICAL FIELD

The present disclosure relates to the technical field of purification, and in particular relates to a filtering device for killing pathogenic microorganisms using deep ultraviolet laser.

BACKGROUND ART

In addition to two ways of droplet transmission and contact transmission, pathogenic microorganisms such as novel coronavirus may also be transmitted through air. Therefore, it is extremely urgent to kill virus in the air, especially for enclosed environment of crowded people, such as carriages, supermarkets, office and entertainment places. For the air purification in the enclosed environment, in an unoccupied situation, the traditional method usually includes a method of employing UV disinfection lamps or spraying disinfectant. However, as the aggravation of COVID-19 and other pandemic situations, these environments also need to be sterilized and disinfected in real time, whereas the traditional air purifier and similar equipment can only adsorb pathogenic microorganisms rather than effectively kill the same. In addition, the installation of the high-power air purification equipment in the large places greatly increases the construction cost, and also causes serious waste of power sources.

In recent years, with rapid development of the laser technology, the application field of the laser technology has become more and more extensive. The research on killing the virus by the laser technology has also received wide attention. At present, the technology for killing pathogenic microorganisms in the gas by using laser still has a series of problems. For example, laser leakage is prone to occurring to cause harm to human bodies. For another example, the energy of laser used in the air is low, thereby leading to poor disinfection and sterilization effects. For further example, laser equipment is high in cost, complex in device, and unable to be replaced and unable to meet all-weather use demands. For another example, secondary pollutants and the like are easily generated.

Therefore, there are urgent-to-be-solved technical problems in this field how to improve the disinfection and sterilization efficiency of the laser in the air, enhance the disinfection and sterilization effect, as well as reduce the cost of laser equipment to enable the laser equipment to meet more use demands and less likely produce secondary pollutants.

SUMMARY

An objective of the present disclosure is to provide a filtering device for killing pathogenic microorganisms using deep ultraviolet laser to solve the problems above. The device not only greatly improves the disinfection and sterilization efficiency of the laser in the air and significantly enhances the disinfection and sterilization effect, but also can be installed in a filter element of an air conditioner or a fan to meet different use demands, thereby the equipment cost is greatly reduced. The device is simple and convenient to use, easy to replace. And deep ultraviolet laser kills the pathogenic microorganisms without generating secondary pollutants, which is capable of meeting all-weather use demands.

To achieve the objective above, a filtering device for killing pathogenic microorganisms using deep ultraviolet laser is provided, which includes: a main body for accommodating gas having the pathogenic microorganisms; and a deep ultraviolet laser module connected to the main body and configured for totally reflecting the deep ultraviolet laser for multiple times to form a deep ultraviolet laser net in the main body, the deep ultraviolet laser module includes a deep ultraviolet laser apparatus and a reflection adjusting assembly, the deep ultraviolet laser apparatus is connected to the main body, and the reflection adjusting assembly arranged at a light-emitting side of the deep ultraviolet laser apparatus is configured for adjusting a density of the deep ultraviolet laser net.

In one embodiment, an inner surface of the main body is of a topological shape.

In one embodiment, the deep ultraviolet laser apparatus has a wavelength ranging between 200 nm and 400 nm.

In one embodiment, the reflection adjusting assembly includes a first reflector, a reflector set, an adjusting part and a support; the adjusting part is rotatably connected to the support; the first reflector is installed on the adjusting part and configured for reflecting the deep ultraviolet laser from the light-emitting side of the deep ultraviolet laser apparatus into the main body; the reflector set is arranged inside the main body, and is configured for totally reflecting the deep ultraviolet laser reflected into the main body by the first reflector for multiple times to form the deep ultraviolet laser net.

In one embodiment, the adjusting part is configured for adjusting an angle of the first reflector, and the angle of the first reflector includes an angle between 40 degrees and 50 degrees.

In one embodiment, the reflector set includes multiple second reflectors arranged on an inner surface of the main body, the multiple second reflectors include an odd number of second reflectors or an even number of second reflectors; when the multiple second reflectors include the odd number of second reflectors, the odd number of second reflectors are distributed at different positions of the inner surface of the main body based on the density of the deep ultraviolet laser net; and when the multiple second reflectors include the even number of second reflectors, the even number of second reflectors are evenly distributed on the inner surface of the main body in a pairwise manner.

In one embodiment, the reflector set includes at least one second reflector completely covering the inner surface of the main body.

In one embodiment, each lens of the reflector set is provided with a reflective film.

In one embodiment, the main body is provided with a light inlet aperture, and the light inlet aperture is configured for transmitting the deep ultraviolet laser into the main body.

In one embodiment, the light inlet aperture includes an annular closed aperture or a polygonal closed aperture.

In accordance with the filtering device for killing the pathogenic microorganisms using deep ultraviolet laser, the deep ultraviolet laser is totally reflected for multiple times by the deep ultraviolet laser module to form a dense and regular deep ultraviolet laser net, such that the gas having the pathogenic microorganisms is filtered in the dense and regular deep ultraviolet laser net, and the pathogenic microorganisms in the gas are killed. The dense and regular deep ultraviolet laser net formed by the filtering device has high laser energy, which can rapidly kill the pathogenic microorganisms in the air, and can kill the pathogenic microorganisms more thoroughly and completely. Therefore, the device not only greatly improves the disinfection and sterilization effect, but also significantly enhances the disinfection and sterilization effect. In addition, the device is simple, safe and efficient, convenient to use, easy to replace, low in manufacturing cost, and free of generating secondary pollutants.

Figure 1:
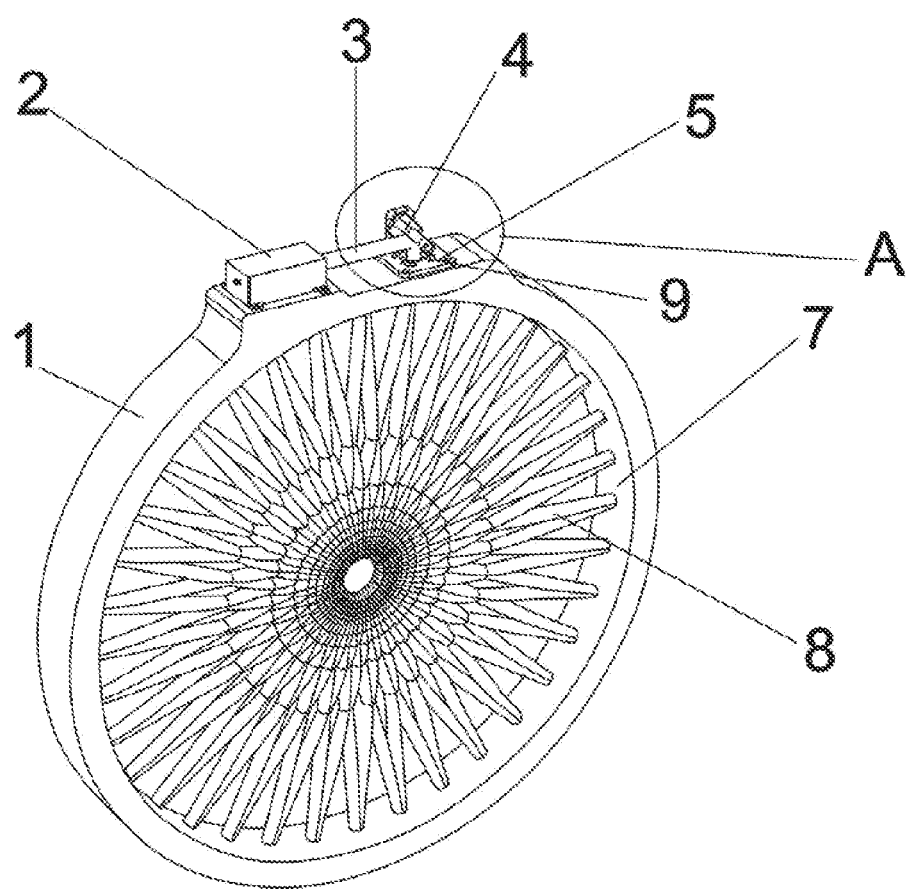
FIG. 1 is a schematic diagram of a filtering device for killing pathogenic microorganisms using deep ultraviolet laser according to an embodiment of the present disclosure.

In the drawings: 1—main body; 2—deep ultraviolet laser apparatus; 3—deep ultraviolet laser; 4—adjusting part; 5—support; 6—first reflector; 7—reflector set; 8—deep ultraviolet laser net; 9—light inlet aperture.

DETAILED DESCRIPTION OF THE EMBODIMENTS

To make the objective, features and advantages of the present disclosure more apparently understandable, the following describes the specific embodiments of the present disclosure in detail with reference to the accompanying drawings. Many specific details are set forth in the following description to facilitate a full understanding of the present disclosure. However, the present disclosure can be implemented in many other ways than those described herein, and those skilled in the art may make similar modifications without departing from the spirit of the present disclosure, and therefore the present disclosure is not to be limited by the specific embodiments disclosed below.

In the description of the present disclosure, it should be understood that the orientation or positional relationship indicated by terms "center", "longitudinal", "transverse", "length", "width", "thickness", "upper", "lower", "front", "back", "left", "right", "vertical", "horizontal", "top", "bottom", "inside", "outside", "clockwise", "counterclockwise", "axial", "radial", "circumferential" is based on the orientation or positional relationship shown in the drawings only for convenience of description of the present disclosure and simplification of description rather than indicating or implying that the device or element referred to must have a particular orientation, be constructed and operate in a particular orientation, and thus not to be construed as a limitation of the present disclosure.

Furthermore, the terms "first" and "second" are used for descriptive purposes only and are not to be construed as indicating or implying relative importance or implying a number of the indicated technical features. As such, the features limited to "first" and "second" may explicitly or implicitly include at least one of those features. In the description of the present disclosure, "a plurality of" means at least two, for example, two, three, and the like, unless expressly specified otherwise.

In the present disclosure, unless expressly specified and defined otherwise, the terms "mounted," "connected," "connection," "fixed" and the like should be understood broadly, for example, may be fixed connection, detachable connection, or integral connection; may be mechanical connection or electrical connection; may be direct connection or indirect connection via an intermediate medium; and may also be internal communication of two elements or an interaction relationship between the two elements, unless expressly defined otherwise. The specific meanings of the above terms in the present disclosure may be understood on a case-by-case basis for those of ordinary skill in the art.

In the present disclosure, unless expressly specified and defined otherwise, the first feature "on" or "under" the second feature may be that the first feature is in direct contact with the second feature, or the first feature is in indirect contact with the second feature via an intermediate medium. Moreover, the first feature "over", "above" and "upside" the second feature may be that the first feature is directly above or diagonally above the second feature, or simply indicates that the first feature is higher than the second feature in a horizontal height. The first feature "under", "below" and "beneath" the second feature may be that the first feature is directly below or diagonally below the second feature, or simply indicates that the first feature is lower than the second feature in a horizontal height.

It is noted that when the element is referred to as being "fixed to" or "arranged on" another element, it may be directly on another element or an intervening element may also be present. When one element is regarded to as being "connected to" another element, it may be directly connected to another element or an intervening element may be present at the same time. The terms "vertical", "horizontal", "upper", "lower", "left", "right" used herein and similar expressions thereof are for illustrative purposes only and are not meant to be the only embodiments.

To make the objective, features and advantages of the present disclosure more apparently understandable, the following further describes the present disclosure in detail with reference to the accompanying drawings and specific embodiments.

Figure 2:
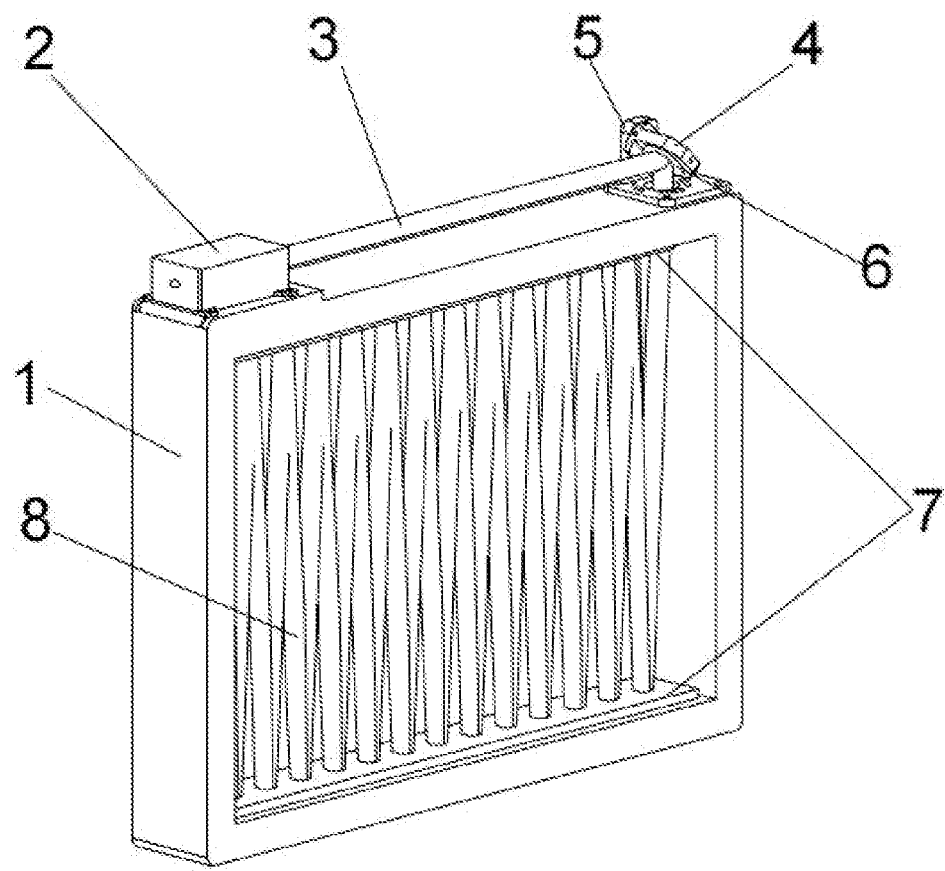
FIG. 2 is another schematic diagram of a filtering device for killing pathogenic microorganisms using deep ultraviolet laser according to an embodiment of the present disclosure.
Figure 3:
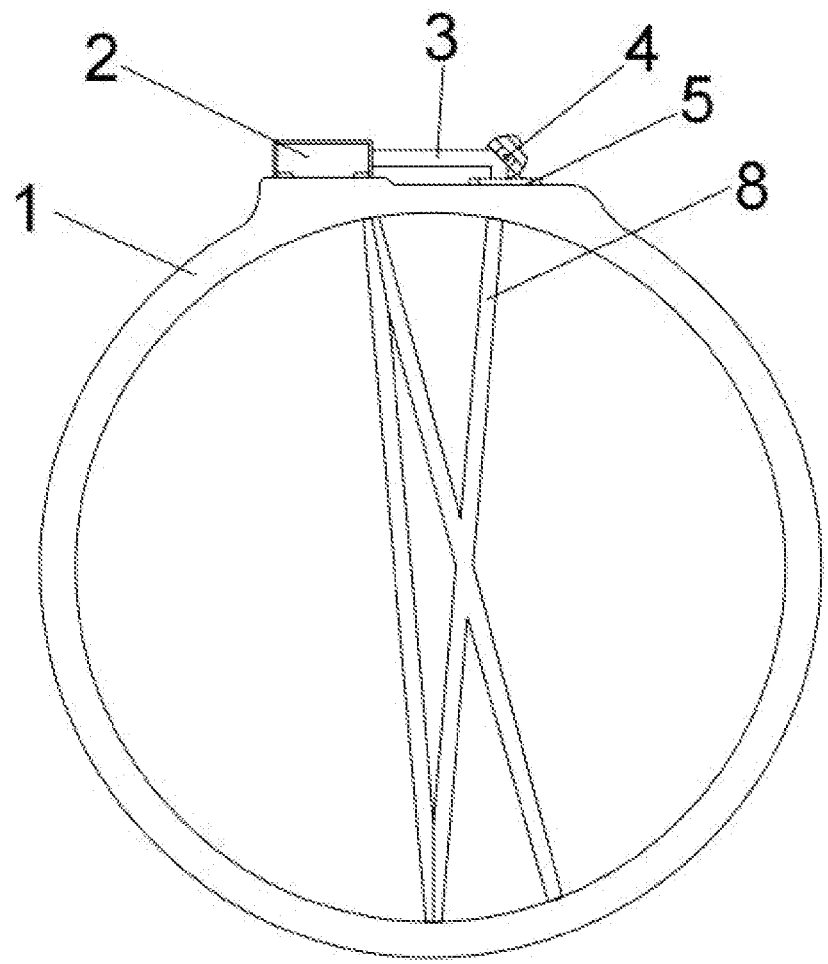
FIG. 3 is a schematic diagram of a path of forming a deep ultraviolet laser net by deep ultraviolet laser in FIG. 1 according to an embodiment of the present disclosure.
Figure 4:
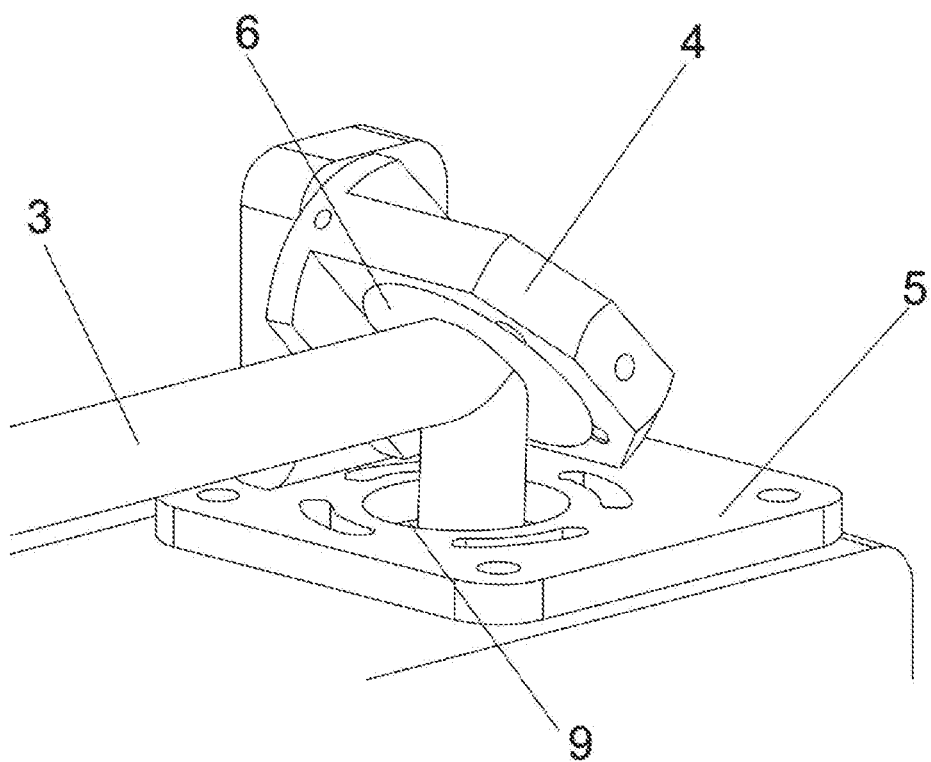
FIG. 4 is a partial enlarged view of detail A in FIG. 1 according to an embodiment of the present disclosure.

As shown in FIG. 1 to FIG. 4, the embodiment provides a filtering device for killing pathogenic microorganisms using deep ultraviolet laser, which includes a main body 1 and a deep ultraviolet laser module.

In an embodiment, the main body 1 is used for accommodating gas having pathogenic microorganisms. In an embodiment, an inner surface of the main body 1 is of a topological shape. The topological shape means that the metric properties such as length, size, area and volume of the shape are not considered, that is, the topological shape can be understood as an arbitrary shape. The topological shape includes, for example, but is not limited to a quad, a pentagon, a square, a rectangle, a circle, a hexagon, a decagon and the like. That is, the shape of the inner surface of the main body 1 includes, for example, but is not limited to the circle, the rectangle, the square and the like.

In an embodiment, the deep ultraviolet laser module is connected to the main body 1 and is used for totally reflecting the deep ultraviolet laser 3 for multiple times to form a dense and regular deep ultraviolet laser net 8, such that the gas is filtered in the dense and regular deep ultraviolet laser net 8 to achieve the killing of the pathogenic microorganisms in the gas. The deep ultraviolet laser net 8 refers to a net formed by totally reflecting laser beams for multiple times. The total reflection refers to a phenomenon that the light is totally reflected back to an original medium when the light emits from an optically denser median to an interface of an optically thinner medium. In an embodiment, a propagation direction of the deep ultraviolet laser 3 can be controlled in a total reflection manner, such that higher deep ultraviolet laser energy can be retained while the deep ultraviolet laser 3 is evenly distributed inside the main body 1. In an embodiment, the dense and regular deep ultraviolet laser net 8 refers to a net formed by the deep ultraviolet laser 3 along a regular reflection path, under the effect of total reflection.

In an embodiment, the deep ultraviolet laser module includes a deep ultraviolet laser apparatus 2 and a reflection adjusting assembly. The deep ultraviolet laser apparatus 2 is connected to the main body 1, and the reflection adjusting assembly is used for adjusting the density of the deep ultraviolet laser net 8.

In an embodiment, the reflection adjusting assembly includes a first reflector 6, a reflector set 7, an adjusting part 4, and a support 5. The adjusting part 4 is rotatably connected to the support 5. The first reflector 6 is installed on the adjusting part 4 and used for reflecting the deep ultraviolet laser 3 into the main body 1. The reflector set 7 is arranged inside the main body 1 and used for totally reflecting the deep ultraviolet laser 3 reflected into the main body for multiple times to form a dense and regular deep ultraviolet laser beam net.

In an embodiment, the reflector set 7 includes multiple second reflectors arranged on the inner surface of the main body 1. When the number of the multiple second reflectors is an odd number, the odd number of second reflectors are distributed at different positions of the inner surface of the main body 1 according to the density of deep ultraviolet laser net 8. When the number of the multiple second reflectors is an even number, the even number of second reflectors are evenly distributed on the inner surface of the main body in a pairwise manner. Further, the reflector set 7 may includes second reflector(s) completely covering the inner surface of the main body 1. In an embodiment, the reflector set 7 includes two second reflectors opposite to each other, the two opposite second reflectors are arranged at the inner surface of the main body 1. For example, in an embodiment, one of the two second reflectors is arranged at one side of the inner surface of the main body which is corresponding to the light inlet aperture 9, and the other one of the two second reflectors is arranged at the opposite side of the inner surface of the main body 1. In an embodiment, the reflector set 7 is a second reflector completely covering the inner surface of the main body 1. In an embodiment, when the reflector set 7 is the second reflector completely covering the inner surface of the main body 1, the formed deep ultraviolet laser net 8 is the laser beam net which is diffused from the center of the inner surface of the main body to the periphery of the inner surface of the main body, such that the formed deep ultraviolet laser beam net is denser and more regular to further enhance the disinfection and sterilization effect.

In an embodiment, each lens of the reflector set 7 is provided with a reflective film. That is, all the lenses of the reflector set 7 are coated with reflective films, and the reflective films are not particularly limited and are commonly used in the art.

In an embodiment, the main body 1 is provided with a light inlet aperture 9 which is used for transmitting the laser into the main body 1.

In an embodiment, the light inlet aperture 9 includes one of an annular closed aperture or a polygonal closed aperture. For example, in an embodiment, the light inlet aperture 9 may be an annular closed aperture, or a hexagonal closed aperture and the like.

In an embodiment, the deep ultraviolet laser apparatus 2 has a wavelength ranging between 200 nm and 400 nm. In an embodiment, the deep ultraviolet laser has high energy per unit area. The wavelength of the deep ultraviolet laser apparatus 2 can be, for example, but not limited to, 257 nm. For example, the wavelength can be 266 nm, and the like. In an embodiment, the deep ultraviolet laser net 8 is completely filled inside the main body 1.

In an embodiment, the deep ultraviolet laser apparatus 2 outputs the deep ultraviolet laser 3. The first reflector 6 is adjusted by rotating the adjusting part 4, such that the output deep ultraviolet laser 3 enters the main body 1 through the light inlet aperture 9 after being reflected by the first reflector 6. Then, the dense and regular deep ultraviolet laser net 8 is formed by totally reflecting laser to intercross multiple times by the reflector set 7 in the main body 1.

In an embodiment, the density of the deep ultraviolet laser net 8 is controlled by adjusting an angle of the first reflector 6 and adjusting the area of the inner surface of the main body covered by the reflector set 7. In general, the larger the area of the inner surface of the main body 1 covered by the reflector set 7, the denser and more regular of the deep ultraviolet laser net 8, so the disinfection and sterilization effect is more stronger. For example, in an embodiment, the angle of the first reflector 6 is adjusted by adjusting (e.g., rotating) the adjusting part 4 to adjust an incident angle of the laser entering the main body 1, thus controlling the density of the deep ultraviolet laser net 8. The angle of the first reflector 6 is an included angle between the support 5 and the first reflector 6, and the angle of the first reflector 6 is adjusted by rotating the adjusting part 4. In an embodiment, the angle of the first reflector 6 includes an angle between 40 degrees and 50 degrees. When the angle of the first reflector 6 ranges between 40 degrees and 50 degrees, the formed deep ultraviolet laser net 8 is denser, thus the disinfection and sterilization effect is greatly enhanced.

In an embodiment, the deep ultraviolet laser apparatus 2 outputs the deep ultraviolet laser 3, and the deep ultraviolet laser 3 has a wavelength of 257 nm. The adjusting part 4 is rotated so that the angle of the first reflector 6 is between 40 degrees and 50 degrees, and the output deep ultraviolet laser 3 enters the main body 1 through the light inlet aperture 9 after being reflected by the first reflector 6. The reflector set 7 includes two second reflectors which are arranged on the inner surface of the main body 1 and opposite to each other. One of the second reflectors is arranged on one side of the inner surface of the main body 1 which is corresponding to the light inlet aperture 9, and the other one of the second reflectors is arranged on the opposite side of the inner surface of the main body 1. Then, the input laser is intercrossed multiple times via the total reflection of the two second reflectors opposite to each other, so as to form the dense and regular deep ultraviolet laser net 8, such that the gas having the pathogenic microorganisms is filtered in the dense and regular deep ultraviolet laser net 8, and the pathogenic microorganisms in the gas are killed. The device greatly improves the disinfection and sterilization efficiency and enhances the disinfection and sterilization effect. Moreover, the device is simple and convenient to use, easy to replace, low in manufacturing cost, and free of generating secondary pollutants.

In an embodiment, the deep ultraviolet laser apparatus 2 outputs the deep ultraviolet laser 3, and the deep ultraviolet laser 3 has a wavelength of 257 nm; the adjusting part 4 is rotated so that the angle of the first reflector 6 is between 40 degrees and 50 degrees, and the output deep ultraviolet laser 3 enters the main body 1 through the light inlet aperture 9 after being reflected by the first reflector 6. The reflector set 7 is a second reflector completely covering the inner surface of the main body 1. That is, the inner surface of the main body 1 is provided with a layer of second reflector. Then, the input laser is intercrossed multiple times via the total reflection of two opposite parts of the second reflector to form the dense and regular deep ultraviolet laser net 8, such that the gas having the pathogenic microorganisms is filtered in the dense and regular deep ultraviolet laser net 8, and the pathogenic microorganisms in the gas are killed. The device greatly improves the disinfection and sterilization efficiency and further enhances the disinfection and sterilization effect. Moreover, the device is simple and convenient to use, easy to replace, low in manufacturing cost, and free of generating secondary pollutants.

The various technical features of the embodiments above may be combined arbitrarily. For simplicity of description, all possible combinations of the various technical features in the embodiments above are not described. However, as long as there is no contradiction, the all possible combinations of the various technical features should be considered as the scope of the present specification. The application field of the technical solution is not specially specified, and for example, the device can be arranged in a traditional air conditioner or an air filter element.

It should be noted that, for those skilled in the art, it is apparent that the present disclosure is not limited to the details of the exemplary embodiments above, and that the present disclosure may be embodied in other specific forms without departing from the spirit or essential characteristics of the present disclosure. Therefore, the embodiments should be regarded as illustrative rather than restrictive in either case. The scope of the present disclosure is defined by the appended claims rather than by the foregoing description, and all changes falling within the meaning and scope of equivalency of the claims are therefore intended to be embraced therein, any reference numerals in the claims shall not be construed as limiting the claims involved.

Specific examples are used for illustration of the principles and implementation of the present disclosure. The description of the embodiments is merely used to help illustrate the method and its core principles of the present disclosure. In addition, a person of ordinary skill in the art can make various modifications in terms of specific implementation and scope of application in accordance with the teachings of the present disclosure. In conclusion, the content of this specification shall not be construed as a limitation to the present disclosure.

What is claimed is:

1. A filtering device for killing pathogenic microorganisms using deep ultraviolet laser, comprising:
    a main body for accommodating gas having the pathogenic microorganisms;
    a deep ultraviolet laser module connected to the main body and configured for totally reflecting the deep ultraviolet laser for a plurality of times to form a deep ultraviolet laser net in the main body, wherein the deep ultraviolet laser module comprises a deep ultraviolet laser apparatus and a reflection adjusting assembly, wherein the deep ultraviolet laser apparatus is connected to the main body, and the reflection adjusting assembly arranged at a light-emitting side of the deep ultraviolet laser apparatus is configured for adjusting a density of the deep ultraviolet laser net; and
    the reflection adjusting assembly comprises a first reflector, a reflector set, an adjusting part and a support; the adjusting part is rotatably connected to the support; the first reflector is installed on the adjusting part and configured for reflecting the deep ultraviolet laser from the light-emitting side of the deep ultraviolet laser apparatus into the main body; the reflector set is arranged inside the main body, and is configured for totally reflecting the deep ultraviolet laser reflected into the main body by the first reflector for a plurality of times to form the deep ultraviolet laser net.

2. The filtering device for killing pathogenic microorganisms using deep ultraviolet laser according to claim 1, wherein an inner surface of the main body is of a topological shape.

3. The filtering device for killing pathogenic microorganisms using deep ultraviolet laser according to claim 1, wherein the deep ultraviolet laser apparatus has a wavelength ranging between 200 nm and 400 nm.

4. The filtering device for killing pathogenic microorganisms using deep ultraviolet laser according to claim 1, wherein the adjusting part is configured for adjusting an angle of the first reflector, and the angle of the first reflector comprises an angle between 40 degrees and 50 degrees.

5. The filtering device for killing pathogenic microorganisms using deep ultraviolet laser according to claim 1, wherein the reflector set comprises a plurality of second reflectors arranged on an inner surface of the main body, the plurality of second reflectors comprise an odd number of second reflectors or an even number of second reflectors; when the plurality of second reflectors comprise the odd number of second reflectors, the odd number of second reflectors are distributed at different positions of the inner surface of the main body based on the density of the deep ultraviolet laser net; and when the plurality of second reflectors comprise the even number of second reflectors, the even number of second reflectors are evenly distributed on the inner surface of the main body in a pairwise manner.

6. The filtering device for killing pathogenic microorganisms using deep ultraviolet laser according to claim 1, wherein the reflector set comprises at least one second reflector completely covering the inner surface of the main body.

7. The filtering device for killing pathogenic microorganisms using deep ultraviolet laser according to claim 1, wherein each lens of the reflector set is provided with a reflective film.

8. The filtering device for killing pathogenic microorganisms using deep ultraviolet laser according to claim 7, wherein the main body is provided with a light inlet aperture, and the light inlet aperture is configured for transmitting the deep ultraviolet laser into the main body.

9. The filtering device for killing pathogenic microorganisms using deep ultraviolet laser according to claim 8, wherein the light inlet aperture comprises an annular closed aperture or a polygonal closed aperture.

* * * * *